United States Patent
Ramstack (12)

(10) Patent No.: US 6,471,995 B1
(45) Date of Patent: Oct. 29, 2002

(54) APPARATUS AND METHOD FOR PREPARING MICROPARTICLES USING LIQUID-LIQUID EXTRACTION

(75) Inventor: J. Michael Ramstack, Lebanon, OH (US)

(73) Assignee: Alkermes Controlled Therapeutics, Inc. II, Cambridge, MA (US)

( * ) Notice: Subject to any disclaimer, the term of this patent is extended or adjusted under 35 U.S.C. 154(b) by 0 days.

(21) Appl. No.: 09/671,426

(22) Filed: Sep. 27, 2000

(51) Int. Cl.$^7$ .............................. A61K 9/14; A61K 9/16; A61K 9/50; B29C 39/10; B01J 13/02
(52) U.S. Cl. ...................... 424/489; 424/490; 424/497; 424/501; 264/4; 264/4.1; 264/4.3; 264/4.33; 264/4.6
(58) Field of Search ................................ 424/489, 490, 424/497, 501; 264/4, 4.1, 4.3, 4.33, 4.6

(56) References Cited

U.S. PATENT DOCUMENTS

| | | | |
|---|---|---|---|
| 4,994,213 A | | 2/1991 | Aitchenson et al. |
| 5,716,526 A | * | 2/1998 | Kelemen et al. ............ 210/650 |
| 6,291,013 B1 | | 9/2001 | Gibson et al. |

FOREIGN PATENT DOCUMENTS

| | | | |
|---|---|---|---|
| WO | WO 95/13799 | * | 5/1995 |
| WO | WO 95/13814 | * | 5/1995 |
| WO | WO 99/25319 A1 | | 5/1999 |

OTHER PUBLICATIONS

B Conti et al., "Use of polylactic acid for the preparation of microparticulate drug delivery systems," J. Microencapsulation, 1992, vol. 9, No. 2, pp. 153–166.

Y.F. MAA et al., "Liquid emulsification by static mixers for use in microencapsulation," J. Microencapsulation, 1996, vol. 13, No. 4, pp. 419–433.

* cited by examiner

Primary Examiner—Thurman K. Page
Assistant Examiner—Todd D Ware
(74) Attorney, Agent, or Firm—Andrea G. Reister; Covington & Burling

(57) ABSTRACT

Method and apparatus for preparing microparticles using liquid-liquid extraction. A first phase and a second phase are combined to form an emulsion. A portion of the second phase is separated from the emulsion (solvent rich), and the solvent is extracted from the separated second phase, which is then returned (solvent poor) to the emulsion. This process of separation of a solvent rich phase, extraction of solvent, and return of a solvent poor phase, is carried out until a selected level of solvent in the emulsion is achieved. Alternatively, the separated solvent rich phase is not returned to the emulsion, but replaced with another solution, such as an aqueous solution, that is free from solvent. The solvent is preferably extracted into an extraction liquid that functions as a "solvent sink" for the solvent.

65 Claims, 7 Drawing Sheets

APPARATUS AND METHOD FOR PREPARING MICROPARTICLES USING LIQUID-LIQUID EXTRACTION

BACKGROUND OF THE INVENTION

1. Field of the Invention

The present invention relates to preparation of microparticles. More particularly, the present invention relates to apparatus and methods for preparing microparticles using liquid extraction of solvent in the emulsion.

2. Related Art

Various methods are known that can encapsulate compounds in the form of microparticles. It is particularly advantageous to encapsulate a biologically active or pharmaceutically active agent within a biocompatible, biodegradable wall forming material (e.g., a polymer) to provide sustained or delayed release of drugs or other active agents. In emulsion-based methods, the material to be encapsulated (drugs or other active agents) is generally dissolved, dispersed, or emulsified in a solvent containing the wall forming material to form a discontinuous phase. The discontinuous phase is combined with a continuous phase to form an emulsion. Solvent is then removed from the emulsion droplets to form the hardened microparticle product.

One approach to solvent removal is to evaporate the solvent, such as by vacuum or heating. One drawback of solvent removal through evaporation is the length of time that is required to remove a sufficient quantity of solvent so that any remaining residual solvent is at an acceptably safe level for use of the microparticles by humans and other animals. The length of time for solvent removal through evaporation can be reduced somewhat by using aqueous extraction of solvent in conjunction with solvent evaporation. An example of such a combined evaporative and aqueous extraction process is described in U.S. Pat. No. 4,389,330. However, such a combined evaporative and aqueous extraction process is not suitable, much less optimal, for solvents that are not amenable to evaporation, such as benzyl alcohol.

Other conventional emulsion-based processes for preparing microparticles rely solely on aqueous extraction of solvent, such as the process described in U.S. Pat. No. 5,407,609. One drawback of aqueous extraction of solvent is the large volume of water that is required. As noted in U.S. Pat. No. 5,407,609, the volume of the extraction medium should be at least the volume needed to dissolve all of the solvent out of the emulsion droplets, such as a volume 10-fold or higher. This problem is particularly acute when the microparticles are being prepared on a commercial scale. Larger and/or more equipment is required to accommodate the large volume of water in the process, resulting in higher equipment and disposal costs.

Thus, there is a need in the art for an improved method and apparatus for preparing microparticles. There is a particular need in the art for an improved process of solvent removal that overcomes the drawbacks of conventional evaporative and aqueous extraction techniques. The present invention, the description of which is fully set forth below, solves the need in the art for such a method and apparatus.

SUMMARY OF THE INVENTION

In one aspect of the present invention, a method of preparing microparticles is provided that comprises the following steps: forming an emulsion, the emulsion comprising a first phase and a second phase, the first phase comprising a polymer, an active agent, and a solvent; separating a portion of the second phase from the emulsion to form a separated second phase; extracting from the separated second phase at least a portion of the solvent present in the separated second phase to form an extracted separated second phase; and returning the extracted separated second phase to the emulsion. The extracting and returning steps may be repeated until a selected level of solvent in the emulsion is reached. The separating step may be carried out by filtering, such as with a membrane filter, the portion of the second phase from the emulsion. The extracting step may be carried out by extracting the solvent into an extraction liquid, which may be miscible with the solvent and a non-solvent for the polymer, the active agent, and the second phase. The extracting step may be carried out in a contactor comprising a hollow fiber. After the returning step, the emulsion may be combined with a quench liquid, such as by transferring the emulsion to a vessel containing the quench liquid, and/or through the use of a static mixer.

In another aspect of the present invention, a method of preparing microparticles is provided that comprises the following steps: forming an emulsion, the emulsion comprising a first phase and a second phase, the first phase comprising a polymer, an active agent, and a solvent; separating a portion of the second phase from the emulsion to form a separated second phase; and replacing the separated second phase in the emulsion with a quantity of a solution. The separating step may be carried out by filtering, such as with a membrane filter, the portion of the second phase from the emulsion. The separating step may be carried out by filtering the second phase from the emulsion using a filter disposed in a diafiltration unit. The separating step may comprise pumping the separated second phase to remove it. The separating step and the replacing step may be performed simultaneously. The separating and replacing steps may be repeated until a selected level of solvent in the emulsion is reached.

In yet a further aspect of the present invention, a method of preparing microparticles is provided that comprises the following steps: forming an emulsion, the emulsion comprising a first phase and a second phase, the first phase comprising a polymer, an active agent, and a solvent; maintaining a separation between the emulsion and an extraction liquid; and extracting the solvent into the extraction liquid. The maintaining step may be carried out by providing a membrane between the emulsion and the extraction liquid. The maintaining step may comprise transferring the emulsion to a vessel fitted with a membrane, the membrane defining a channel disposed in the vessel. The extracting step may be carried out by allowing the solvent to diffuse from the emulsion across the membrane into the channel. The extracting step may be repeated until a selected level of solvent in the emulsion is reached.

In yet another aspect of the present invention, a system for preparing microparticles is provided. The system comprises a first vessel configured to contain an emulsion. The first vessel includes a filter that separates the first vessel into a first portion and a second portion. A contactor, comprising a hollow fiber, is in fluid communication with the first portion and with the second portion of the first vessel. A second vessel, configured to contain an extraction liquid, is in fluid communication with the contactor. A first pump is configured to pump the extraction liquid through the contactor to extract solvent from a continuous phase of the emulsion. A second pump is configured to pump the continuous phase through the contactor.

In still a further aspect of the present invention, a system for preparing microparticles is provided. The system comprises a vessel configured to contain an emulsion. A membrane is disposed in the vessel, the membrane defining a channel in the vessel. A pump is configured to pump an extraction liquid through the channel to extract solvent from a continuous phase of the emulsion.

Features and Advantages

A feature of the present invention is that solvent is extracted from the emulsion phase prior to quenching. The extraction is performed more slowly than conventional aqueous extraction processes that need to be performed quickly.

A feature of the present invention is that a portion of the continuous phase is separated from the emulsion, solvent is extracted from that portion, which is then returned to the emulsion. The extraction and return process is repeated until a selected level of solvent in the emulsion is reached.

It is a further feature of the present invention that it can be carried out using a non-aqueous extraction liquid, such as heptane or octamethylcyclotetrasiloxane (OMCTS).

Still a further feature of the present invention is that extraction of the solvent can be carried out using a hollow fiber contactor.

Yet a further feature of the present invention is that extraction of the solvent can be carried out in the vessel containing the emulsion by allowing the solvent to diffuse across a membrane fitted into the vessel.

An advantage of the present invention is that it reduces the volume of quench liquid, typically water for injection (WFI) that is required.

The present invention advantageously overcomes disposal problems found in conventional aqueous extraction processes. Firstly, the process of the present invention uses a reduced volume of liquid overall so there is less volume to be disposed. Secondly, a non-aqueous extraction liquid such as heptane can be disposed of cleanly and efficiently through burning. Thus, the cost of disposal is reduced.

Another advantage of the reduced volume of liquid in the process is that smaller scale equipment and less quench liquid can be used to produce a given batch size of microparticles than with a conventional aqueous extraction process. With smaller water requirements, larger batch sizes may be produced using the same equipment and WFI capacity.

BRIEF DESCRIPTION OF THE FIGURES

The present invention is described with reference to the accompanying drawings. In the drawings, like reference numbers indicate identical or functionally similar elements.

DETAILED DESCRIPTION OF THE PREFERRED EMBODIMENTS

Overview

Figure 1:
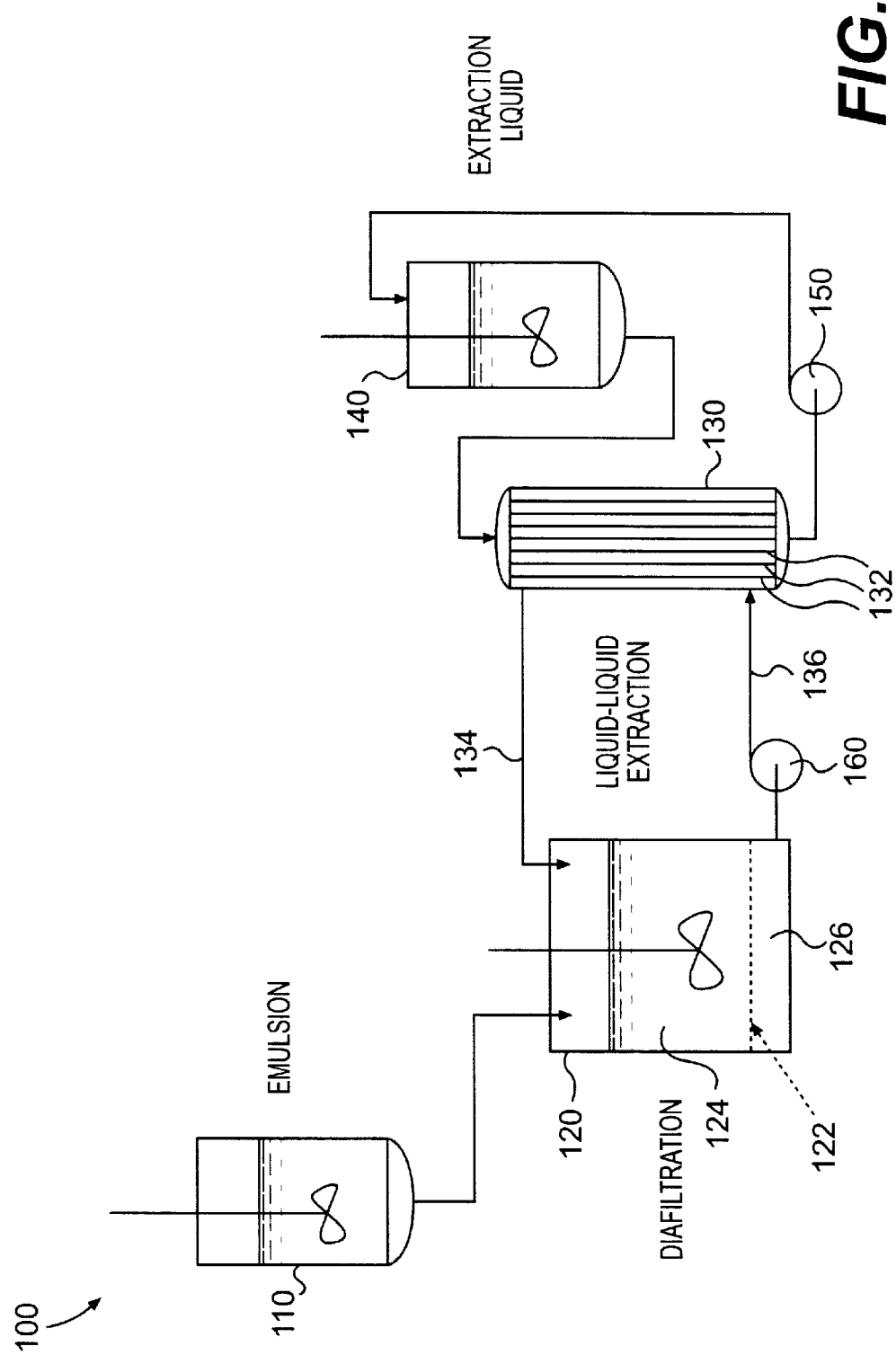
FIG. 1 illustrates one embodiment of the apparatus of the present invention for preparing microparticles by liquid-liquid extraction using a contactor.

The process of the present invention overcomes the deficiencies and drawbacks of conventional processes for preparing microparticles. Particularly, the process of the present invention overcomes the drawbacks in conventional processes of solvent removal. In the process of the present invention, a first or discontinuous phase is formed that preferably comprises a polymer, an active agent, and a solvent. A second or continuous phase is combined with the first phase to form an emulsion. A portion of the second phase is separated from the emulsion (solvent rich), and the solvent is extracted from the separated second phase, which is then returned (solvent poor) to the emulsion. This process of separation of a solvent rich phase, extraction of solvent, and return of a solvent poor phase, is carried out until a selected level of solvent in the emulsion is achieved. Alternatively, the separated solvent rich phase is not returned to the emulsion, but replaced with another solution, such as an aqueous solution, that is free from solvent. In another aspect of the present invention, a separation is maintained between the emulsion and an extraction liquid, and the solvent is extracted into the extraction liquid. In such a process, a membrane can be used to separate the emulsion and the extraction liquid, and extraction is carried out by allowing the solvent to diffuse across the membrane into the extraction liquid.

In the present invention, solvent extraction is preferably carried out by extraction of the solvent into a non-aqueous extraction liquid that functions as a "sink" for the solvent. The extraction liquid is preferably a non-solvent for the polymer, active agent, and water, but freely miscible with the solvent. Such an extraction liquid acts as a sink for the solvent so that it can be removed from the emulsion, thereby allowing the emulsion droplets to form into microparticles. Because the solubility of the solvent in the extraction liquid is high, it provides a driving force for transport of the solvent out of the emulsion droplet, through the continuous phase, and into the extraction liquid. One suitable extraction liquid is heptane, which advantageously can be disposed of at the end of the process by burning. Another suitable extraction liquid is octamethylcyclotetrasiloxane (OMCTS), available from Dow coming as 244 Fluid. Other suitable extraction liquids would be readily apparent to one skilled in the art, and it should be understood that the present invention is not limited to any particular extraction liquid.

To ensure clarity of the description that follows, the following definitions are provided. By "microparticles" or "microspheres" is meant solid particles that contain an active agent or other substance dispersed or dissolved within a polymer that serves as a matrix or binder of the particle. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per hundred parts total weight of microparticle. For example, 10 wt.% active agent would mean 10 parts active agent by weight and 90 parts polymer by weight. Unless otherwise indicated to the contrary, percentages (%) reported herein are by weight. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

Methods and Apparatus of the Present Invention

Turning now to the accompanying drawings, the methods and apparatus of the present invention will be described. With reference to FIG. 1, a system 100 is shown for preparing microparticles in accordance with one embodiment of the present invention. System 100 includes a vessel 110 containing an emulsion. The emulsion comprises a first phase and a second phase. In a preferred embodiment of the invention, the first phase comprises a polymer, an active agent, and a solvent. Alternatively, the first phase may comprise a polymer and a solvent. The second phase is preferably an aqueous phase, comprising an aqueous solution. The emulsion can be formed using techniques well known to one skilled in the art. A particularly preferred technique for forming the emulsion is through the use of a static mixer. A process for forming an emulsion using a static mixer is described, for example, in U.S. Pat. No. 5,654,008, the entirety of which is incorporated herein by reference. The phase comprising the active agent and the polymer may be referred to herein as the "organic phase". The other phase may be referred to herein as the "continuous phase".

The emulsion is transferred to a diafiltration vessel 120. A membrane filter 122 is disposed in diafiltration vessel 120, so that diafiltration vessel 120 is separated into a first portion 124 and a second portion 126. The "solvent rich" aqueous phase of the emulsion is separated from the emulsion into second portion 126 by membrane filter 122. A pump 160 is used to pump the separated aqueous phase from diafiltration vessel 120 into a contactor 130, so that contactor 130 is in fluid communication with second portion 126 via a flow path 136.

Figure 7:
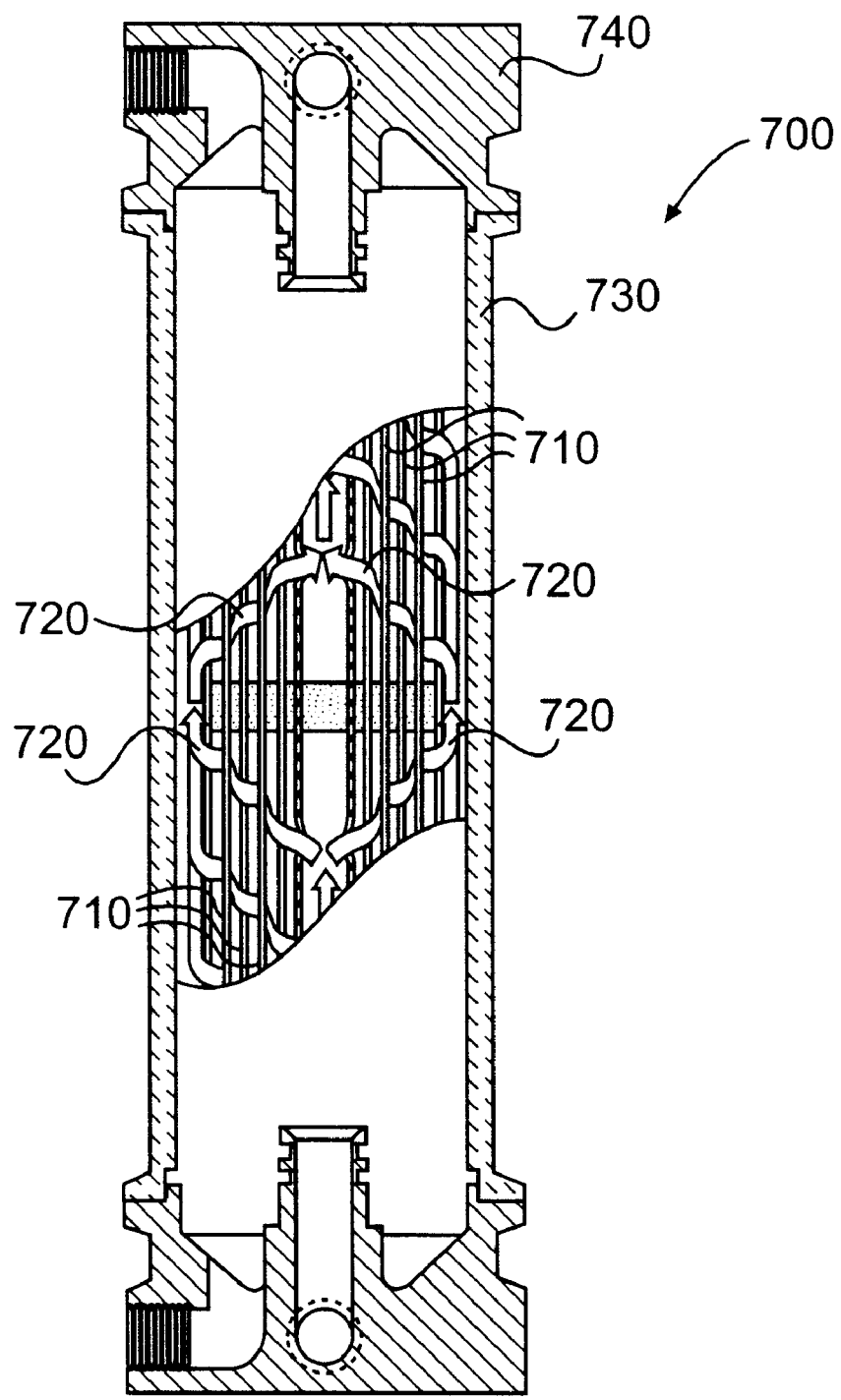
FIG. 7 shows an exemplary embodiment of a membrane contactor suitable for preparing microparticles in accordance with the present invention.

Extraction of solvent present in the separated aqueous phase into an extraction liquid (liquid-liquid extraction or "LLE") takes place in contactor 130. In a preferred embodiment of the present invention, contactor 130 is a membrane contactor that comprises a plurality of hollow fibers, such as fibers 132. A particularly preferred membrane contactor is a Liqui-Cel® membrane contactor available from Celgard LLC, Charlotte, N.C. A membrane contactor 700 is shown in more detail in FIG. 7. Membrane contactor 700 includes a membrane cartridge 730 disposed in a housing 740. Membrane cartridge 730 includes a plurality of hollow fibers 710 through which liquid can flow. Liquid can also flow external to fibers 710, as illustrated by flow paths 720. A suitable material for fibers 710 is polypropylene. Suitable fibers 710 include polypropylene microporous hollow fibers with a 300 micron OD, 240 micron ID, effective pore size of 0.03 micron, approximately 40% porosity, and a surface area of approximately 1.4 $m^2$. Other suitable fiber material and configuration would be readily apparent to one skilled in the art.

In one embodiment of the present invention, the separated aqueous phase is passed through fibers 710, while extraction liquid is passed through flow paths 720. Alternatively, the separated aqueous phase may be passed through flow paths 720, and the extraction liquid passed through fibers 710. As shown in FIG. 1, the extraction liquid is pumped from a vessel 140 via a pump 150 through contactor 130.

After flowing through contactor 130, the separated aqueous phase is returned to diafiltration vessel 120, so that contactor 130 is in fluid communication with first portion 124 via a flow path 134. The separated aqueous phase that flows into contactor 130 via flow path 136 is "solvent rich" in comparison with the "solvent poor" separated aqueous phase that flows out of contactor 130 via flow path 134 because solvent has been extracted out of the separated aqueous phase in contactor 130 into an extraction liquid. The flow through contactor 130 of the separated aqueous phase and the extraction liquid is continued until a selected level of solvent in the emulsion is reached.

A preferred extraction liquid of the present invention functions as a "sink" for the solvent used in the emulsion. Preferably, the extraction liquid is a non-solvent for the polymer, active agent (if present), and water, but freely miscible with the solvent. An extraction liquid suitable for use in the present invention is heptane. Another extraction liquid suitable for use is octamethylcyclotetrasiloxane (OMCTS), available from Dow coming as 244 Fluid. Other suitable extraction liquids would be readily apparent to one skilled in the art.

Figure 2:
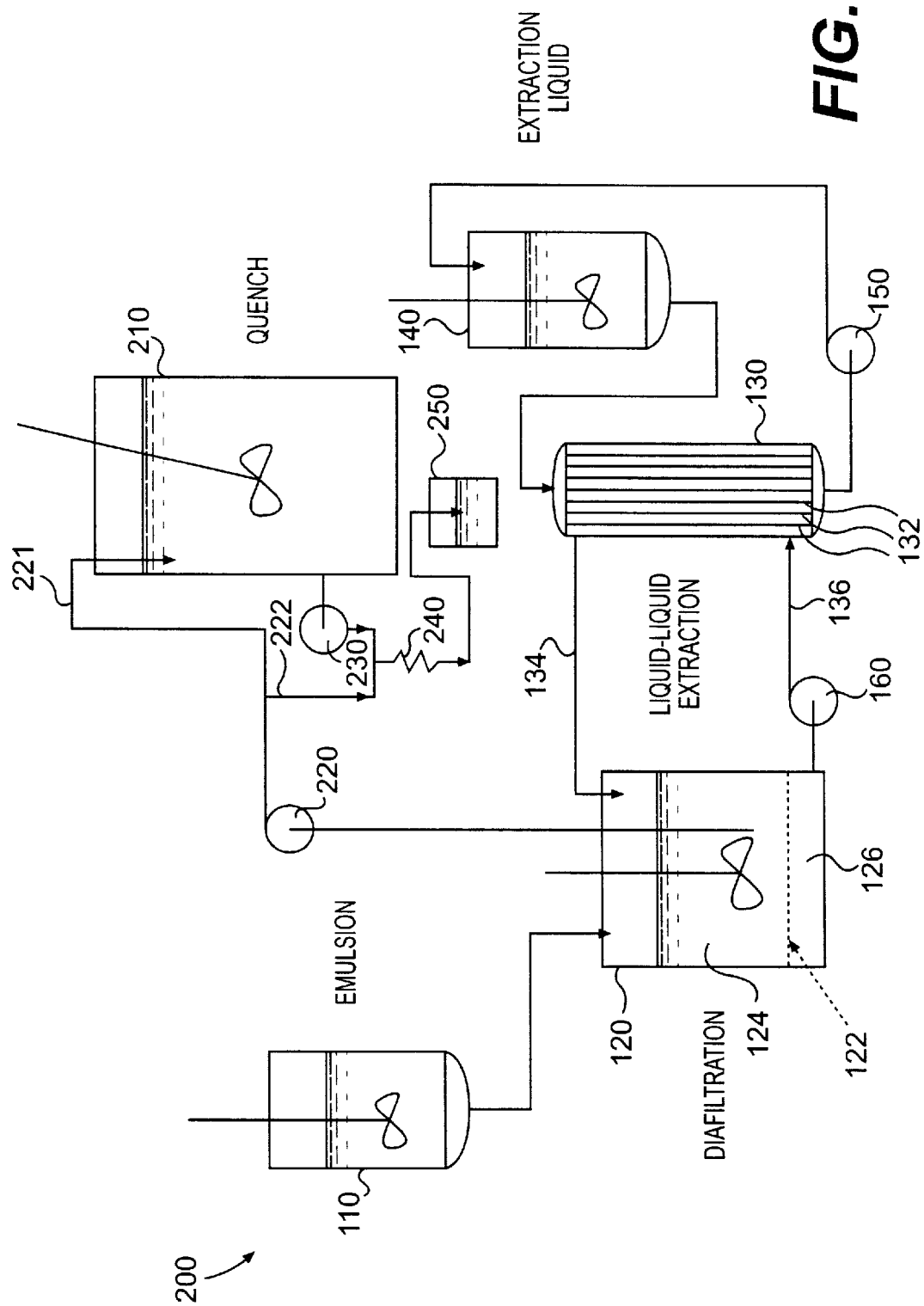
FIG. 2 illustrates another embodiment of the apparatus of the present invention or preparing microparticles by liquid-liquid extraction using a contactor.

Turning now to FIG. 2, another embodiment of the apparatus of the present invention for preparing microparticles by liquid-liquid extraction using a contactor is shown. A system 200 is shown that includes emulsion vessel 110, diafiltration vessel 120, contactor 130, and vessel 140 for the extraction liquid, which operate in a manner similar to that described above for FIG. 1. Such description will not be repeated here for brevity. Once a selected level of solvent in the emulsion is reached, the emulsion is transferred out of diafiltration vessel 120 via a pump 220 so that the emulsion can be combined with a quench liquid to complete hardening and precipitation of microparticles. The selected level of solvent may be the desired level of solvent for the resulting microparticles. Alternatively, the selected level of solvent may be greater than the desired level, with additional solvent extraction to take place via the quench liquid. The quench liquid is preferably an aqueous solution, but other types of quench liquids may be used. In one embodiment of the present invention, the emulsion is transferred via a flow path 221 to a quench vessel 210 that includes a quench liquid. In such an embodiment, the microparticles harden and precipitate in quench vessel 210.

In another embodiment of the present invention, the emulsion and the quench liquid are combined in a static mixer 240. In such an embodiment, the emulsion is pumped into static mixer 240 by pump 220, as shown via a flow path 222. The quench liquid is pumped into static mixer 240 by a pump 230. The outflow from static mixer 240 flows into an end vessel 250 in which the microparticles harden and precipitate.

A static or motionless mixer consists of a conduit or tube in which is received a number of static mixing elements. Static mixers provide uniform mixing in a relatively short length of conduit, and in a relatively short period of time. With static mixers, the fluid moves through the mixer, rather than some part of the mixer, such as a blade, moving through the fluid. A static mixer suitable for use with the present invention is more fully described in U.S. Pat. No. 4,511,258, the entirety of which is incorporated herein by reference.

The hardened microparticles are recovered, washed, and dried using techniques well known to one skilled in the art. The microparticles can also be sieved or otherwise separated by size in a well known manner.

Figure 3:
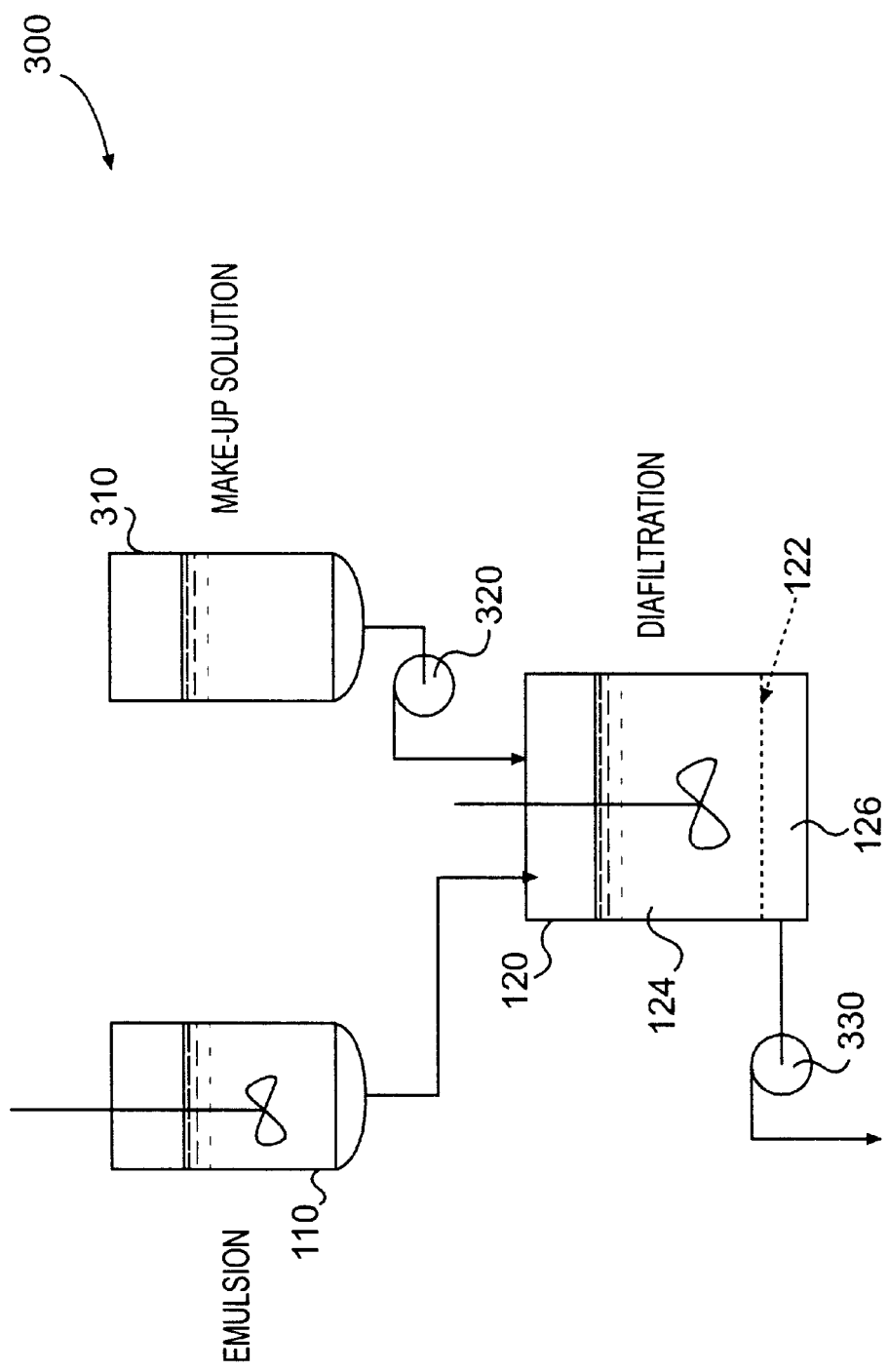
FIG. 3 illustrates one embodiment of the apparatus of the present invention for preparing microparticles by liquid-liquid extraction using a diafiltration unit.

Turning now to FIG. 3, another embodiment of the apparatus of the present invention for preparing microparticles by liquid-liquid extraction using a diafiltration unit is shown. In a manner similar to that described above with respect to FIGS. 1 and 2, an emulsion is prepared and transferred to diafiltration vessel 120 that is fitted with membrane filter 122. The solvent rich aqueous phase of the emulsion diffuses across membrane filter 122 into second portion 126 of diafiltration vessel 120. In a system 300 shown in FIG. 3, a pump 330 is used to remove the solvent rich aqueous phase from second portion 126. Preferably, the separated solvent rich aqueous phase is disposed of in a safe manner known to one skilled in the art.

The separated solvent rich aqueous phase is replaced by a make-up solution that is pumped via a pump 320 from a vessel 310 into diafiltration vessel 120. The make-up solution is preferably water, an aqueous solution, or another liquid that is free from solvent. The microparticles harden and participate in diafiltration vessel 120, from which they can be recovered and dried. In a preferred embodiment of the present invention, the separating of the solvent rich aqueous phase from the emulsion, such as by pumping it out of second portion 126, is performed simultaneously with replacing with the make-up solution, such as by pumping make-up solution into diafiltration vessel 120. The separating and replacing steps are carried out until a selected level of solvent in the emulsion is reached.

Figure 4:
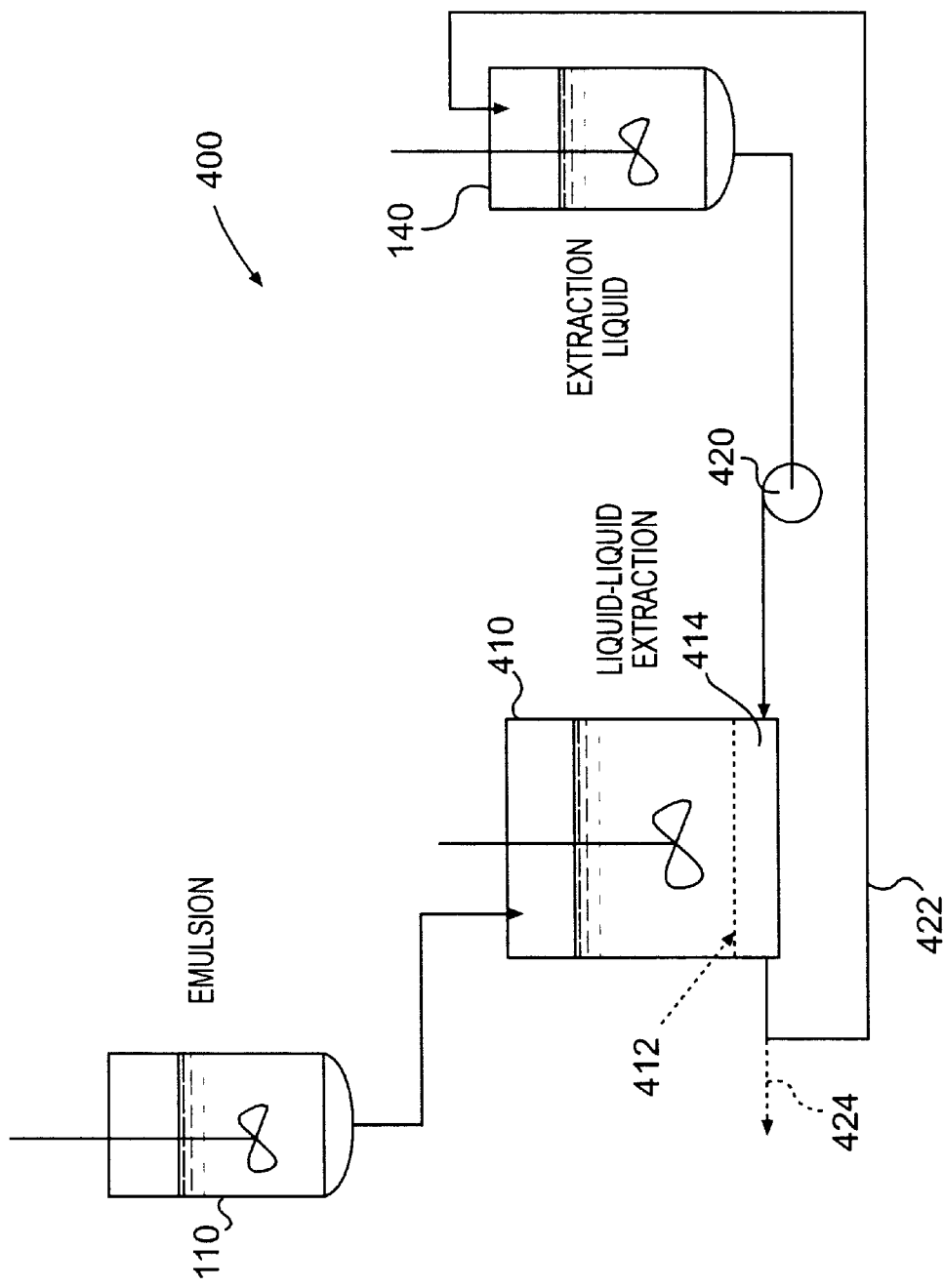
FIG. 4 illustrates one embodiment of the apparatus of the present invention for preparing microparticles by liquid-liquid extraction using a vessel having a channel.

Turning now to FIG. 4, one embodiment of the apparatus of the present invention for preparing microparticles by liquid-liquid extraction using a vessel having a channel is shown. As can be seen from FIG. 4, a system 400 includes emulsion vessel 110 from which the emulsion is transferred into a liquid-liquid extraction ("LLE") vessel 410. LLE vessel 410 is configured with a flow through channel 414 and a membrane 412. Extraction liquid is pumped via a pump 420 from vessel 140 into and through channel 414. Extraction liquid can be recirculated through channel 414, as shown by the flow path designated by 422. Alternatively, extraction liquid can be pumped through channel 414 in an outflow or a "single pass" configuration, as shown by the flow path designated by 424. Solvent present in the emulsion diffuses across membrane 412 into the extraction liquid flowing through channel 414. The solvent is removed from LLE vessel 410 as the extraction liquid flows out via flow path 424 and/or flow path 422. In the embodiment illustrated in FIG. 4, extraction occurs in LLE vessel 410 without the need for filtrating the aqueous phase of the emulsion.

Figure 5:
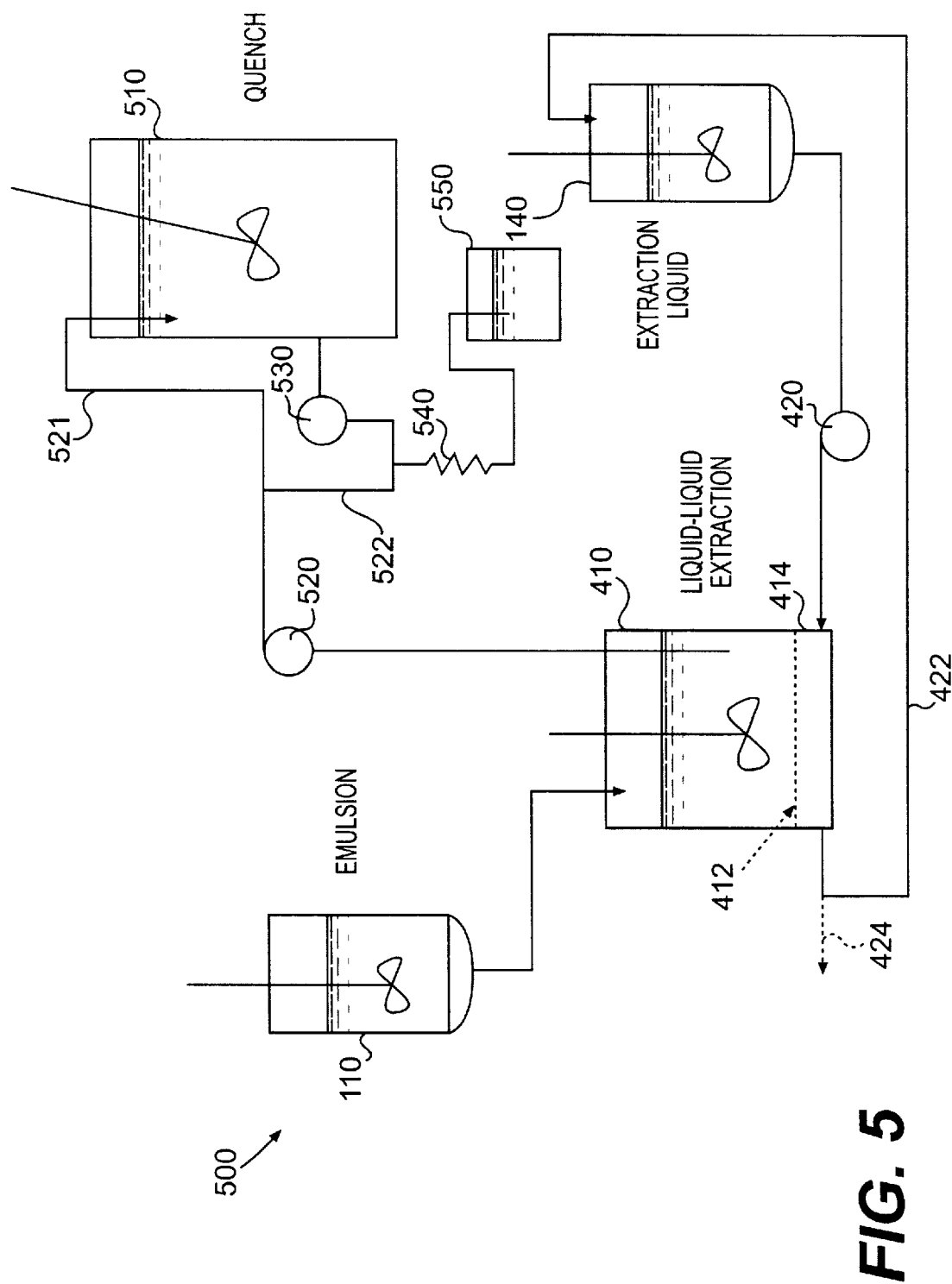
FIG. 5 illustrates another embodiment of the apparatus of the present invention for preparing microparticles by liquid-liquid extraction using a vessel having a channel.

Turning now to FIG. 5, another embodiment of the apparatus of the present invention for preparing microparticles by liquid-liquid extraction using an LLE vessel is shown. A system 500 is shown that includes emulsion vessel 110, LLE vessel 410, and vessel 140 for the extraction liquid, which operate in a manner similar to that described above for FIG. 4. Such description will not be repeated here for brevity. Once a selected level of solvent in the emulsion is reached, the emulsion is transferred out of LLE vessel 410 via a pump 520 so that the emulsion can be combined with a quench liquid to complete hardening and precipitation of microparticles. The quench liquid is preferably an aqueous solution, but other types of quench liquids may be used. In one embodiment of the present invention, the emulsion is transferred via a flow path 521 to a quench vessel 510 that includes a quench liquid. In such an embodiment, the microparticles harden and precipitate in quench vessel 510.

In another embodiment of the present invention, the emulsion and the quench liquid are combined in a static mixer 540. In such an embodiment, the emulsion is pumped into static mixer 540 by pump 520, as shown by a flow path 522. The quench liquid is pumped into static mixer 540 by a pump 530. The outflow from static mixer 540 flows into an end vessel 550 in which the microparticles harden and precipitate.

A number of solvent partitioning experiments were conducted to characterize the effectiveness of LLE. In these experiments, known amounts of water and extraction liquid (heptane or silicone oil) were mixed. Various amounts of the solvents for the polymer in the emulsion (ethyl acetate, benzyl alcohol, or methylene chloride) were added to the water and extraction liquid mixture to form a combined mixture. After thorough mixing for several hours, the combined mixture was separated into water and extraction liquid fractions, i.e., a water fraction and a heptane fraction, and a water fraction and a silicone oil fraction. The solvent content, i.e., the content of ethyl acetate, benzyl alcohol, and methylene chloride, of each fraction was analyzed by gas chromatography. The resulting data were plotted to produce an equilibrium curve for the concentration of the solvent in the water fraction versus the concentration of the solvent in the extraction liquid fraction. A graph of the concentration of solvent in extraction liquid as a function of the concentration of solvent in water is shown in FIG. 6.

Figure 6:
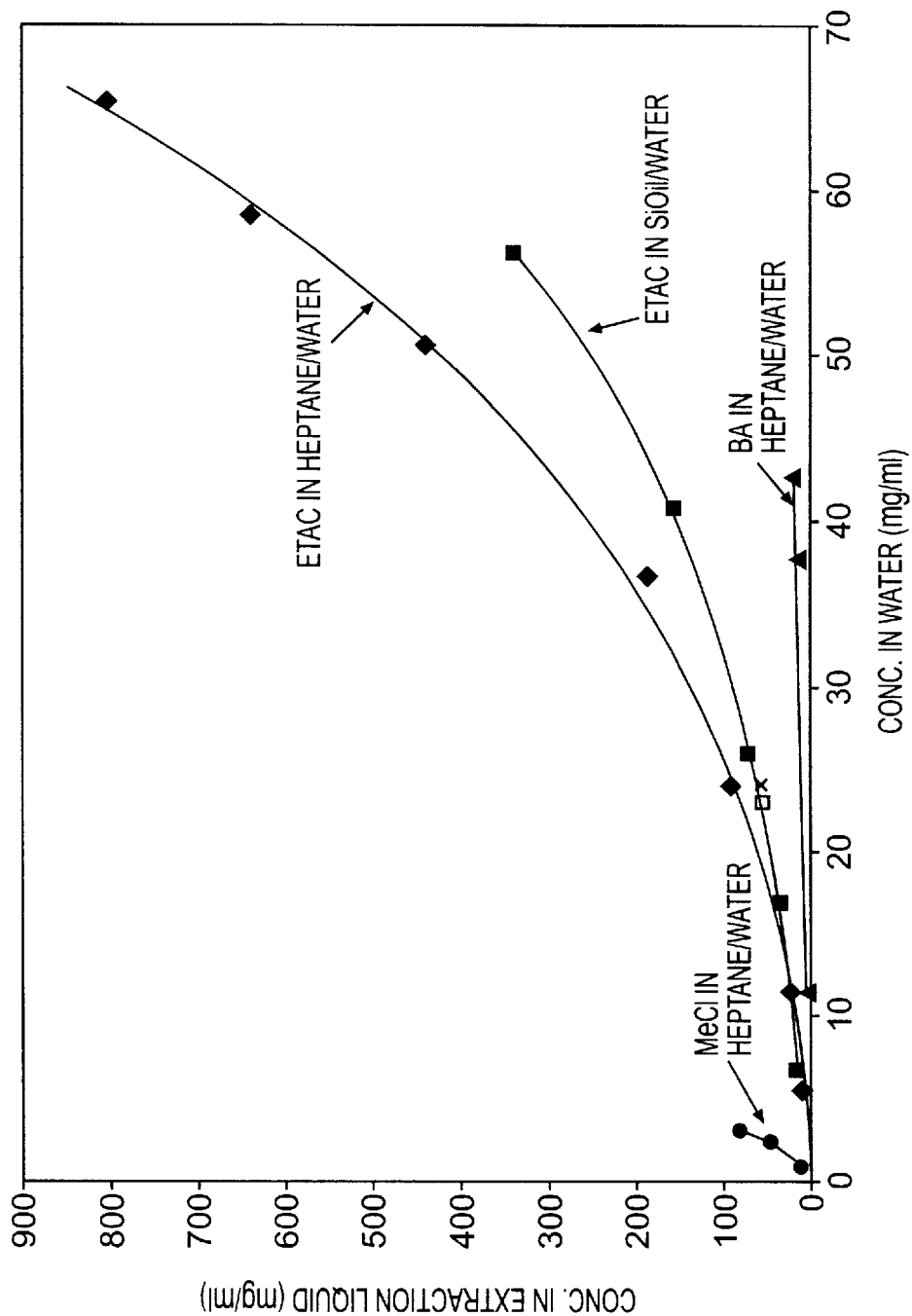
FIG. 6 depicts a graph of the concentration of solvent in extraction liquid as a function of the concentration of solvent in water, illustrating that liquid-liquid extraction is most effective at higher aqueous concentrations.

The results depicted in FIG. 6 show that methylene chloride (MeCl) partitions the best into heptane, followed by ethyl acetate (ETAC). Benzyl alcohol (BA) partitions poorly into heptane. Notably, MeCl and ETAC are freely miscible with heptane, while BA has a very low solubility in heptane. Silicone oil appears to perform similarly, but not as well as heptane for extracting ETAC from water. The data in FIG. 6 also show that LLE is most efficient when aqueous concentrations of solvent are high. In other words, the capacity of the extraction liquid for the solvent is greater at higher aqueous concentrations. For example, the equilibrium concentration of ETAC in heptane (about 600 mg/ml) is approximately ten times the concentration in water at 60 mg/ml. At an aqueous concentration of 10 mg/ml, the equilibrium concentration of ETAC in heptane is about 20 mg/ml, only two times the concentration in water. Therefore, it is preferable to carry out the LLE process on the emulsion where aqueous concentrations are high, rather than, for example, in a quench solution where the aqueous concentrations are lower. The data in FIG. 6 also suggest that LLE becomes less efficient as the concentration of solvent in the emulsion droplet or microparticle decreases. Therefore, a final quench step may be required to finish extraction of the solvent, such as is shown above in FIGS. 2 and 5. However, it should be readily apparent to one skilled in the art that the volume of quench liquid that may be required in the embodiments depicted in FIGS. 2 and 5 is considerably less than that required with conventional processes.

EXAMPLES

The following examples are provided to explain the invention, and to describe the materials and methods used in carrying out the invention. The examples are not intended to limit the invention in any manner.

Examples 1–3

Examples 1–3 were carried out using an experimental setup substantially as shown in FIG. 1, and described as follows. A 2 L glass jacketed stirred cell reactor fitted with a 2" Teflon impeller was used for emulsion formation. The drain of the emulsion vessel was connected by silicone tubing to the diafiltration vessel. The 2 L diafiltration vessel, Amicon Model 2000 (Millipore, Bedford, Mass.) was fitted with a 20μ stainless steel screen on the bottom of the vessel. The filtrate port of the diafiltration vessel was coupled by silicone tubing and a peristaltic pump to the shell side of a polypropylene microporous hollow fiber membrane contactor, Celgard Liqui-Cel® 2.5×8 Membrane Contactor (Celgard, Charlotte, N.C.). The outlet from the membrane contactor is routed back to the diafiltration vessel via silicone tubing. In a concurrent fashion, heptane is recirculated through the fiber side of the membrane contactor via Viton tubing and a peristaltic pump. The heptane was contained in a 2 L glass beaker with a magnetic stirrer.

Example 1

9.2% Ibuprofen Microparticles 10.24 gm of Medisorb® 7525 PLG polymer, 0.82 IV were dissolved in 60.1 gm of ethyl acetate. To this solution was dissolved 1.04 gm of ibuprofen (Sigma). This solution was then added to the emulsion vessel containing 1L of a 1% PVA (DuPont Elvanol, Grade 51-05) aqueous solution and 60.2 gm of ethyl acetate. This mixture was stirred at approximately 500 RPM for several minutes to form an emulsion. The emulsion was then transferred to the diafiltration vessel and stirred at medium speed. Heptane and filtrate flow were then initiated each at 200 mL/min.

After 10 minutes the oil phase droplets of the emulsion were noticeably darker when observed microscopically. After 30 minutes, the suspension was rinsed by exchanging several volumes of DI water through the diafiltration vessel. Microparticles were recovered on a 45μ sieve screen and dried by forcing ambient air up through the bed under a laboratory hood. After drying for at least 24 hours, the material was recovered. Yield was 5.8 gm of generally good quality microparticles although somewhat sticky. Based on final ethyl acetate content in the heptane (GC), 95.2 gm or 79% of the ethyl acetate was transferred from the emulsion to the heptane. Drug content (HPLC) of the microparticles was 8.1% indicating an 88% encapsulation efficiency. Residual ethyl acetate content (GC) was 5.3%.

Example 2

33% Ibuprofen Microparticles 2 gm of ibuprofen (Sigma) was dissolved in 28 gm of polymer solution composed of 14.2(w/w) % of Medisorb® 7525 PLG polymer, 0.82 IV in ethyl acetate. This solution was added to the emulsion vessel containing an aqueous solution composed of 1L of 1% PVA and 59.4 gm of ethyl acetate. This mixture was stirred at approximately 500 RPM for several minutes to form an emulsion. The emulsion was then transferred to the diafiltration vessel and stirred at medium speed. Heptane and filtrate flow were then initiated each at 200 mL/min.

After 60 minutes, the suspension was rinsed by exchanging 2L of cold DI water in the diafiltration vessel. The suspension was then pumped out on to a 45μ sieve screen and the microparticles rinsed with additional DI water. The microparticles were then dried overnight in a laboratory hood.

Yield was 2.6 gm. Based on final ethyl acetate content in heptane 64.2 gm or 77% of the ethyl acetate was transferred from the emulsion to the heptane phase. Drug content (HPLC) of the microparticles was 27.5% or 83% encapsulation efficiency. Residual ethyl acetate content (GC) was 4.1%.

Example 3

40% Risperidone Microparticles 6 gm of Medisorb® 7525 PLG polymer, 0.82 IV were dissolved in 29.9 gm of ethyl acetate. 4 gm of Risperidone (Janssen Pharmaceutica, Beerse, Belgium) were dissolved in 13 gm of benzyl alcohol. The polymer and drug solutions were blended and then added to the emulsion vessel containing 1L of 1% PVA and 59.7 gm of ethyl acetate. The mixture was stirred at approximately 500 RPM for several minutes to form an emulsion. The emulsion was then transferred to the diafiltration vessel and filtrate and heptane flow initiated at 200 ml/min. The stainless steel screen in the diafiltration vessel was replaced with a Whatman #41 filter.

After 5 minutes the oil phase droplets appeared to have darkened. Because of filter fouling problems the experiment was terminated at 26 minutes. Several volumes of cold DI water were exchanged in the diafilter and the microparticles were recovered on a 20μ sieve screen and additionally rinsed with approximately 4L of cold DI water. The material was allowed to dry overnight in a laboratory hood. Yield was 3.5 gm. 58 gm or 64% of the ethyl acetate was transferred to the heptane phase, while only 3.8 gm or 29% of the benzyl alcohol was transferred. Drug content of the microparticles was 25.8% (65% encapsulation efficiency). Residual ethyl acetate and benzyl alcohol contents were 2.1% and 7.4%, respectively.

Examples 4–8

Examples 4–8 were carried out using an experimental setup substantially as shown in FIG. 3, and described as follows. A 2L glass jacketed stirred cell reactor fitted with a 2" Teflon impeller was used as an emulsion vessel. The emulsion vessel was coupled to a 2L stirred diafiltration vessel (Amicon Model 2000) via silicone tubing. The diafiltration filter was composed of Porox 1/16" porous support disk. Downstream from the diafiltration vessel, the filtrate is pumped out to waste via silicone tubing and a peristaltic pump. Make-up solution contained in an adjacent vessel is coupled to the diafiltration vessel via silicone tubing and a peristaltic pump.

Example 4

40% Risperidone Microparticles 6 gm of Medisorb® 7525 PLG polymer, 0.82 IV were dissolved in 29.9 gm of ethyl acetate. Similarly, 4 gm of Risperidone (Janssen Pharmaceutica, Beerse, Belgium) were dissolved in 13 gm of benzyl alcohol. These two solutions were blended then added to the emulsion vessel containing 1L of 1% PVA and 59.5 gm of ethyl acetate. The emulsion was formed by stirring at approximately 500 RPM for several minutes. The emulsion was then transferred to the diafiltration vessel. The filtrate and replacement solution (DI water) pumps were each started at 100 mL/min. After 2 minutes the oil phase droplets appeared darker. After 30 minutes the microparticles appeared well formed. At 45 minutes the microparticles were recovered on a 20μ screen and dried via passage of cold air (~9° C.) through the microparticle bed for several days. Yield was 3.9 gm. Drug content of the microparticles was measured at 30.5%, (76% encapsulation efficiency). Residual ethyl acetate and benzyl alcohol contents were 2.2% and 5.4%, respectively.

Example 5

40% Risperidone Microparticles 5.9 gm of Medisorb(® 7525 PLG polymer, 0.82 IV were dissolved in 30.1 gm of ethyl acetate. Likewise 4 gm of Risperidone (Janssen Pharmaceutica, Beerse, Belgium) were dissolved in 13 gm of benzyl alcohol. The two solutions were then blended and added to the emulsion vessel containing 1L of 1% PVA and 59.9 gm of ethyl acetate. An emulsion was formed by stirring for several minutes at approximately 500 RPM. The emulsion was then transferred to the diafiltration vessel and flow started (filtrate and replacement pumps at 100 ml/min). The replacement solution was made up of 1% PVA. After 10 minutes the oil phase droplets became noticeably darker. After 60 minutes round well-defined microparticles were formed. Material was recovered on a 20$\mu$ screen, rinsed with DI water and dried via passage of cold air through the microparticle bed. Yield was 4.6 gm. Drug content of the microparticles was measured at 29.7% (74% encapsulation efficiency). Residual ethyl acetate and benzyl alcohol contents were 2.1% and 5.8%, respectively.

Example 6

40% Ibuprofen Microparticles 6.0 gm of Medisorb® 7525 PLG polymer, 0.82 IV were dissolved in 40.1 gm of ethyl acetate. To this solution was dissolved 4.05 gm of ibuprofen. This solution was then added to the emulsion formed by stirring for several minutes at approximately 500 RPM. The emulsion was then transferred to the diafiltration vessel and flow started (filtrate and replacement pumps at 100 ml/min). The replacement solution was DI water. After 10 minutes the oil phase droplets appeared noticeably darker. After 60 minutes the microparticles were recovered on a 20$\mu$ stainless steel screen and dried via cold air as in the previous example. Yield was 6.0 gm. Drug content of the microparticles was 33.7% (84% encapsulation efficiency). Residual ethyl acetate content was 2.6%.

Example 7

40% Ibuprofen Microparticles 6.0 gm of Medisorb® 7525 PLG polymer, 0.82 IV were dissolved in 40 gm of ethyl acetate. To this solution was dissolved 4.03 gm of ibuprofen. This solution was then added to the emulsion vessel containing 1L of 1% PVA and 60 gm of ethyl acetate. An emulsion was formed by stirring for several minutes at approximately 500 RPM. The emulsion was then chilled to 8.7° C. via recirculating chilled glycol solution in the vessel jacket. The emulsion was then transferred to the diafiltration vessel and flow started (filtrate and replacement pumps at 100 ml/min). The replacement solution was chilled (4.8° C.) DI water. After 60 minutes the suspension was recovered on a 20$\mu$ screen and dried as before using cold air. Yield was 6.5 gm. Drug content of the microparticles was 37.0% (93% encapsulation efficiency). Residual ethyl acetate content was 4.2%.

Example 8

20% Ibuprofen Microparticles 8.0 gm of Medisorb® 7525 PLG polymer, 0.82 IV were dissolved in 40.3 gm of ethyl acetate. To this solution was dissolved 2.17 gm of ibuprofen. This solution was then added to the emulsion vessel containing 1L of 1% PVA and 60.0 gm of ethyl acetate. An emulsion was formed by stirring for several minutes at approximately 500 RPM. The emulsion was then transferred to the diafiltration vessel and flow started (filtrate and replacement pumps at 100 ml/min). The replacement solution was DI water. After 15 minutes the oil phase droplets appeared noticeably darker. After 45 minutes the microparticles were recovered and washed in 5L of chilled DI water. After 2 hours the microparticles were recovered onto a 20$\mu$ screen and dried via passage of cold (5.5–12.0° C.) air overnight.

Yield 7.2 gm. Drug content of the microparticles was measured at 18% (90% encapsulation efficiency). Residual ethyl acetate content was 3.3%.

Examples 9–11

Examples 9–11 were carried out using an experimental setup substantially as shown in FIG. 4, and described as follows. A 2L glass jacketed stirred cell reactor fitted with a 2″ Teflon impeller was used as the emulsion vessel. The emulsion vessel was coupled to a stirred-cell liquid-liquid extraction vessel (LLE vessel 410 depicted in FIG. 4). The volume of the LLE vessel was approximately 2L. At the base of the LLE vessel was a polypropylene microporous membrane (Celgard® 2400) positioned over a helical channel for heptane flow. Heptane was recirculated through the channel from an external vessel via Viton tubing and a peristaltic pump.

Example 9

20% Ibuprofen Microparticles 8.12 gm of Medisorb® 7525 PLG polymer, 0.82 IV was dissolved in 41.3 gm of ethyl acetate. To this solution was dissolved 2.04 gm of ibuprofen. This solution was then added to the emulsion vessel containing 1L of 1% PVA and 60.7 gm of ethyl acetate. An emulsion was formed by stirring for several minutes at approximately 500 RPM. The emulsion was then transferred to the LLE stirred-tank vessel. Heptane flow was initiated at 100 ml/min.

At 20 minutes the oil droplet phase became noticeably darker. After 120 minutes the suspension was transferred to a 5L stirred water wash at 8° C. After 2 hours the microparticles were collected on a 20$\mu$ screen and dried via passage of chilled air overnight as before. Yield was 6.04 gm. Drug content of the microparticles was measured at 4.6% (23% encapsulation efficiency). Residual ethyl acetate content was 6.6%.

Example 10

10% Ibuprofen Microparticles 9.12 gm of Medisorb(® 7525 PLG polymer, 0.82 IV was dissolved in 41.4 gm of ethyl acetate. To this solution was dissolved 1.01 gm of ibuprofen. This solution was then added to the emulsion vessel containing 1L of 1% PVA and 60.0 gm of ethyl acetate. An emulsion was formed by stirring for several minutes at approximately 500 RPM. The emulsion was then transferred to the LLE stirred-tank vessel. Heptane flow was initiated at 100 ml/min.

After 2 hours the suspension was transferred to a 5L water wash (~5° C.). After 2 hours the microparticles were recovered on a 20$\mu$ screen and dried via passage of chilled air overnight as before. Yield was 8.05 gm. Drug content of the microparticles was measured at 4.8% (48% encapsulation efficiency). Residual ethyl acetate content was 7.1%.

Example 11

20% Ibuprofen Microparticles 8.34 gm of Medisorb® 7525 PLG polymer, 0.82 IV was dissolved in 60.4 gm of methylene chloride. To this solution was dissolved 2.04 gm of ibuprofen. This solution was then added to the emulsion vessel containing 1L of 1% PVA. An emulsion was formed by stirring for several minutes at approximately 500 RPM. The emulsion was then transferred to the LLE stirred-tank vessel. Heptane flow was initiated at 100 ml/min.

At 60 minutes the oil phase droplets were noticeably darker. After 120 minutes the suspension was transferred to 5L stirred water (~8° C.). After 2 hours the material was collected on a 20μ sieve screen and dried overnight at ~6° C. Yield was 7.6 gm. Drug content of the microparticles was 7.0% (35% encapsulation efficiency). Residual methylene chloride content was 4.1%.

Microparticles made in accordance with the present invention preferably comprise a polymeric binder. Suitable polymeric binder materials include poly(glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, albumin, casein, and waxes. Poly (d,l-lactic-co-glycolic acid) is commercially available from Alkermes, Inc. (Blue Ash, OH). A suitable product commercially available from Alkermes, Inc. is a 50:50 poly(d,l-lactic-co-glycolic acid) known as MEDISORB (5050 DL. This product has a mole percent composition of 50% lactide and 50% glycolide. Other suitable commercially available products are MEDISORB® 6535 DL, 7525 DL, 8515 DL and poly(d,l-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,l-PLA (Resomer® RG 206), and from Birmingham Polymers (Birmingham, Alabama). These copolymers are available in a wide range of molecular weights and ratios of lactic acid to glycolic acid.

One type of microparticle that can be prepared using the methods of the present invention is a sustained-release microparticle that is biodegradable. However, it should be understood by one skilled in the art that the present invention is not limited to biodegradable or other types of sustained-release microparticles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is useful in according multiphasic release patterns.

The microparticles may include an active agent or other type of substance that is released from the microparticles into the host. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one ("risperidone") and 3-[2-[4-(6-fluro-1,2-benzisoxazol-3-yl)-1-piperidinyl]ethyl]-6,7,8,9-tetrahydro-9-hydroxy-2-methyl-4H-pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-Parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodienone, meperidine, morphine and the like; non-narcotics such as salicylates, aspirin, acetaminophen, d-propoxyphene and the like; opioid receptor antagonists, such as naltrexone and naloxone; antibiotics such as gentamycin, tetracycline and penicillins; anti-cancer agents; anticonvulsants; antiemetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs.

Still other suitable active agents include estrogens, antibacterials; antifungals; antivirals; anticoagulants; anticonvulsants; antidepressants; antihistamines; and immunological agents.

Other examples of suitable biologically active agents include peptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antipyretic and analgesic agents; antitussives and expectants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and heparin; hemostatic agents such as thrombin, menadione sodium bisulfite and acetomenaphthone; antituberculous agents such as isoniazide and ethanbutol; hormones such as prednisolone sodium phosphate and methimazole.

Conclusion

While various embodiments of the present invention have been described above, it should be understood that they have been presented by way of example only, and not limitation. The present invention is not limited to controlled release microparticles, nor is it limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents.

What is claimed is:

1. A method of preparing microparticles, comprising:
   forming an emulsion, the emulsion comprising a first phase that comprises a polymer, an active agent, and a solvent, and a second phase;
   separating a portion of the second phase from the emulsion to form a separated second phase;
   extracting from the separated second phase at least a portion of the solvent present in the separated second phase to form an extracted separated second phase; and
   returning the extracted separated second phase to the emulsion.

2. The method of claim 1, further comprising:
   repeating the extracting and returning steps until a selected level of solvent in the emulsion is reached.

3. The method of claim 1, wherein the separating step is carried out by filtering the portion of the second phase from the emulsion.

4. The method of claim 3, wherein the filtering is carried out using a membrane filter.

5. The method of claim 1, further comprising prior to the separating step:
   transferring the emulsion to a diafiltration unit.

6. The method of claim 5, wherein the separating step is carried out by filtering the second phase from the emulsion using a filter disposed in the diafiltration unit.

7. The method of claim 1, wherein the extracting step is carried out by extracting the solvent into an extraction liquid.

8. The method of claim 7, wherein the extraction liquid is miscible with the solvent and is a non-solvent for the polymer, the active agent, and the second phase.

9. The method of claim 7, wherein the extracting step is carried out in a contactor comprising a hollow fiber.

10. The method of claim 9, wherein the extraction liquid flows through the hollow fiber and the second phase is external to the hollow fiber.

11. The method of claim 9, wherein the second phase flows through the hollow fiber and the extraction liquid is external to the hollow fiber.

12. The method of claim 6, wherein the extracting step is carried out by extracting the solvent into an extraction liquid.

13. The method of claim 12, wherein the extraction liquid is miscible with the solvent and is a non-solvent for the polymer, the active agent, and the second phase.

14. The method of claim 12, wherein the extracting step is carried out in a contactor comprising a hollow fiber.

15. The method of claim 14, wherein the extraction liquid flows through the hollow fiber and the second phase is external to the hollow fiber.

16. The method of claim 14, wherein the second phase flows through the hollow fiber and the extraction liquid is external to the hollow fiber.

17. The method of claim 1, further comprising after the returning step:
   combining the emulsion with a quench liquid.

18. The method of claim 17, wherein the combining step comprises transferring the emulsion to a vessel containing the quench liquid.

19. The method of claim 17, wherein the combining step is carried out using a static mixer.

20. The method of claim 7, wherein the extraction liquid comprises heptane.

21. The method of claim 7, wherein the extraction liquid comprises octamethylcyclotetrasiloxane.

22. The method of claim 1, wherein the active agent is selected from the group consisting of risperidone, 9-hydroxyrisperidone, and pharmaceutically acceptable salts thereof.

23. The method of claim 22, wherein the solvent comprises benzyl alcohol and ethyl acetate.

24. The method of claim 1, wherein the polymer is selected from the group consisting of poly(glycolic acid), poly-d,1-lactic acid, poly-1-lactic acid, and copolymers of the foregoing.

25. The method of claim 7, wherein the active agent is selected from the group consisting of risperidone, 9-hydroxyrisperidone, and pharmaceutically acceptable salts thereof.

26. The method of claim 25, wherein the solvent comprises benzyl alcohol and ethyl acetate.

27. The method of claim 25, wherein the polymer is selected from the group consisting of poly(glycolic acid), poly-d,1-lactic acid, poly-1-lactic acid, and copolymers of the foregoing.

28. The method of claim 1, wherein the active agent is ibuprofen.

29. The method of claim 7, wherein the active agent is ibuprofen.

30. The method of claim 29, wherein the extraction liquid comprises heptane.

31. A method of preparing microparticles, comprising:
   forming an emulsion, the emulsion comprising a first phase that comprises a polymer, an active agent, and a solvent, and a second phase;
   separating a portion of the second phase from the emulsion to form a separated second phase; and
   replacing the separated second phase in the emulsion with a quantity of a solution.

32. The method of claim 31, wherein the separating step is carried out by filtering the portion of the second phase from the emulsion.

33. The method of claim 32, wherein the filtering is carried out using a membrane filter.

34. The method of claim 31, further comprising prior to the separating step:

transferring the emulsion to a diafiltration unit.

35. The method of claim 34, wherein the separating step is carried out by filtering the second phase from the emulsion using a filter disposed in the diafiltration unit.

36. The method of claim 31, wherein the separating step comprises pumping the separated second phase to remove it.

37. The method of claim 34, wherein the separating step comprises pumping the separated second phase to remove it from the diafiltration unit.

38. The method of claim 31, wherein the separating step and the replacing step are performed simultaneously.

39. The method of claim 35, wherein the separating step and the replacing step are performed simultaneously.

40. The method of claim 37, wherein the separating step and the replacing step are performed simultaneously.

41. The method of claim 31, wherein the active agent is selected from the group consisting of risperidone, 9-hydroxyrisperidone, and pharmaceutically acceptable salts thereof.

42. The method of claim 41, wherein the solvent comprises benzyl alcohol and ethyl acetate.

43. The method of claim 41, wherein the polymer is selected from the group consisting of poly(glycolic acid), poly-d,1-lactic acid, poly-1-lactic acid, and copolymers of the foregoing.

44. The method of claim 31, further comprising:

repeating the separating and replacing steps until a selected level of solvent in the emulsion is reached.

45. The method of claim 31, wherein the solution is an aqueous solution.

46. A method of preparing microparticles, comprising:

forming an emulsion, the emulsion comprising a first phase that comprises a polymer, an active agent, and a solvent, and a second phase;

maintaining a separation between the emulsion and an extraction liquid; and extracting the solvent into the extraction liquid.

47. The method of claim 46, further comprising:

repeating the extracting step until a selected level of solvent in the emulsion is reached.

48. The method of claim 46, wherein the maintaining step is carried out by providing a membrane between the emulsion and the extraction liquid.

49. The method of claim 48, wherein the extracting step is carried out by allowing the solvent to diffuse across the membrane into the extraction liquid.

50. The method of claim 46, wherein the extraction liquid is miscible with the solvent and is a non-solvent for the polymer, the active agent, and the second phase.

51. The method of claim 46, further comprising after the extracting step:

combining the emulsion with a quench liquid.

52. The method of claim 51, wherein the combining step comprises transferring the emulsion to a vessel containing the quench liquid.

53. The method of claim 51, wherein the combining step is carried out using a static mixer.

54. The method of claim 46, wherein the extraction liquid comprises heptane.

55. The method of claim 46, wherein the extraction liquid comprises octamethylcyclotetrasiloxane.

56. The method of claim 46, wherein the active agent is selected from the group consisting of risperidone, 9-hydroxyrisperidone, and pharmaceutically acceptable salts thereof.

57. The method of claim 56, wherein the solvent comprises benzyl alcohol and ethyl acetate.

58. The method of claim 46, wherein the polymer is selected from the group consisting of poly(glycolic acid), poly-d,1-lactic acid, poly-1-lactic acid, and copolymers of the foregoing.

59. The method of claim 46, wherein the maintaining step comprises:

transferring the emulsion to a vessel fitted with a membrane, the membrane defining a channel disposed in the vessel.

60. The method of claim 59, wherein the extracting step is carried out by allowing the solvent to diffuse from the emulsion across the membrane into the channel.

61. The method of claim 59, further comprising:

introducing the extraction liquid into the channel.

62. The method of claim 60, further comprising:

introducing the extraction liquid into the channel.

63. A method of preparing microparticles, comprising:

forming an emulsion, the emulsion comprising a first phase that comprises a polymer and a solvent, and a second phase;

separating a portion of the second phase from the emulsion to form a separated second phase;

extracting from the separated second phase at least a portion of the solvent present in the separated second phase to form an extracted separated second phase; and returning the extracted separated second phase to the emulsion.

64. A method of preparing microparticles, comprising:

forming an emulsion, the emulsion comprising a first phase that comprises a polymer and a solvent, and a second phase;

separating a portion of the second phase from the emulsion to form a separated second phase; and replacing the separated second phase in the emulsion with a quantity of a solution.

65. A method of preparing microparticles, comprising:

forming an emulsion, the emulsion comprising a first phase that comprises a polymer and a solvent, and a second phase;

maintaining a separation between the emulsion and an extraction liquid; and extracting the solvent into the extraction liquid.

* * * * *